US010532025B2

(12) United States Patent
Duesterberg et al.

(10) Patent No.: US 10,532,025 B2
(45) Date of Patent: *Jan. 14, 2020

(54) INTRAUTERINE DELIVERY SYSTEM FOR CONTRACEPTION

(71) Applicant: Bayer Oy, Turku (FI)

(72) Inventors: Bernd Duesterberg, Oberkrämer ot Bärenklau (DE); Manja Ahola, Plikklo (FI); Jyrki Pihlaja, Paimio (FI); Heikki Lyytikäinen, Naantali (FI); Harri Jukarainen, Kuusisto (FI); Satu Kleemola, Naantali (FI); Tero Parkatti, Turku (FI); Tuula Valo, Turku (FI); Ina Gröticke, Berlin (DE); Bernhard Lindenthal, Berlin (DE); Ulrike Fuhrmann, Berlin (DE)

(73) Assignee: Bayer Oy, Turku (FI)

( * ) Notice: Subject to any disclaimer, the term of this patent is extended or adjusted under 35 U.S.C. 154(b) by 0 days.

This patent is subject to a terminal disclaimer.

(21) Appl. No.: 15/984,310

(22) Filed: May 18, 2018

(65) Prior Publication Data

US 2018/0263899 A1    Sep. 20, 2018

Related U.S. Application Data

(63) Continuation of application No. 13/934,913, filed on Jul. 3, 2013, now Pat. No. 9,999,592, which is a continuation of application No. 12/995,905, filed as application No. PCT/FI2009/050598 on Jul. 1, 2009, now abandoned.

(30) Foreign Application Priority Data

Jul. 3, 2008  (EP) ..................................... 08397516

(51) Int. Cl.
| | | |
|---|---|---|
| A61K 9/00 | (2006.01) | |
| A61K 31/195 | (2006.01) | |
| A61K 31/196 | (2006.01) | |
| A61K 31/565 | (2006.01) | |
| A61K 31/567 | (2006.01) | |
| A61K 31/57 | (2006.01) | |
| A61K 31/58 | (2006.01) | |
| A61K 45/06 | (2006.01) | |
| A61K 31/569 | (2006.01) | |

(52) U.S. Cl.
CPC .......... *A61K 9/0039* (2013.01); *A61K 31/195* (2013.01); *A61K 31/196* (2013.01); *A61K 31/565* (2013.01); *A61K 31/567* (2013.01); *A61K 31/569* (2013.01); *A61K 31/57* (2013.01); *A61K 31/58* (2013.01); *A61K 45/06* (2013.01)

(58) Field of Classification Search
CPC .................................................. A61K 9/0039
See application file for complete search history.

(56) References Cited

U.S. PATENT DOCUMENTS

| | | | |
|---|---|---|---|
| 3,880,991 | A | 4/1975 | Yolles |
| 4,188,951 | A | 2/1980 | Higuchi et al. |
| 6,440,445 | B1 | 8/2002 | Nowak et al. |
| 2004/0247674 | A1 | 12/2004 | Haapakumpu et al. |

FOREIGN PATENT DOCUMENTS

| | | | | |
|---|---|---|---|---|
| CN | 1931113 | | 3/2007 | |
| EP | 0024780 | | 3/1981 | |
| EP | 0024781 | | 3/1981 | |
| EP | 0024779 | | 10/1984 | |
| EP | 0330786 | | 9/1989 | |
| EP | 0117163 | | 8/1997 | |
| FI | 94947 | | 12/1996 | |
| FR | 2539027 | | 7/1984 | |
| JP | 2003-221338 | | 8/2003 | |
| WO | 1996/001092 | | 1/1996 | |
| WO | 1998/005323 | | 2/1998 | |
| WO | 1998/014169 | | 4/1998 | |
| WO | 1999/010412 | | 3/1999 | |
| WO | 2000/000550 | | 1/2000 | |
| WO | 2000/029464 | | 5/2000 | |
| WO | 2003/017971 | | 3/2003 | |
| WO | WO-03017971 | A1 * | 3/2003 | ........... A61K 9/0024 |
| WO | 2004/096151 | | 11/2004 | |
| WO | 2005/021750 | | 3/2005 | |
| WO | 2006/028431 | | 3/2006 | |
| WO | WO-2006106180 | A1 * | 10/2006 | ............. A61F 6/144 |
| WO | 2006/121969 | | 11/2006 | |

OTHER PUBLICATIONS

USPTO, Non-final Office Action for U.S. Appl. No. 15/650,846, dated Nov. 2, 2018, 16 pages.
USPTO, Final Office Action for U.S. Appl. No. 15/650,846, dated May 17, 2018, 15 pages.
Swedish Patent Office, International Search Report for International Patent Application No. PCT/FI2009/050598, dated Oct. 9, 2009, 8 pages.
Swedish Patent Office, Written Opinion for International Patent Application No. PCT/FI2009/050598, dated Oct. 9, 2009, 11 pages.
Swedish Patent Office, International Preliminary Report on Patentability for International Patent Application No. PCT/FI2009/050598, dated Sep. 28, 2010, 15 pages.
Andersson, et al., "Levonorgestrel-releasing intrauterine device in the treatment of menorrhagia", Br J Obstet Gynaecol. 97(8), Aug. 1990, pp. 690-694.

(Continued)

*Primary Examiner* — Susan T Tran
*Assistant Examiner* — William Craigo
(74) *Attorney, Agent, or Firm* — IP Spring

(57) ABSTRACT

The invention relates to a method for contraception and for reducing menstrual problems and inducing amenorrhea, wherein an intrauterine delivery device is used for the controlled release of a combination of progestogen or a drug having a progestogenic activity and at least one therapeutically active substance capable of preventing or suppressing abnormal and/or irregular endometrial bleeding over a prolonged period of time.

21 Claims, 4 Drawing Sheets

(56) References Cited

OTHER PUBLICATIONS

Beaumont, et al., "Danazol for heavy menstrual bleeding", Cochrane Database Syst Rev., Issue 2. Art. No. CD001017, 2002, 14 pages.
Becker, et al., "Endostatin inhibits the growth of endometriotic lesions but does not affect fertility", Fertility and Sterility, vol. 84, Suppl. 2, Oct. 2005, pp. 1144-1155.
Bilian, "Chinese experience with intrauterine devices", Biliam Contraception, 75, 2007, pp. S31-S34.
Bongers, et al., "Current treatment of dysfunctional uterine bleeding", Maturitas 47(3), 2004, pp. 159-174.
Cameron, et al., "The Effects of Danazol, Mefenamic Acid, Norethisterone and a Progesterone-Impregnated Coil on Endometrial Prostaglandin Concentrations in Women with Menorrhagia", Prostaglandins, vol. 34, No. 1, Jul. 1987, pp. 99-110.
Campana, et al., "traitement medical des menorragies: revue de la litterature", Medicine & Hygiene, vol. 57, No. 2266, Sep. 1, 1999, pp. 1585-1590.
European Patent Office, European Search Report for European Patent Application No. 08397516, dated Nov. 17, 2014, 2 pages.
European Patent Office, Examination Report for European Patent Application No. 09772630.1, dated Feb. 27, 2015, 5 pages.
European Patent Office, European Search Report for European Patent Application No. 14193392.9, dated Jun. 25, 2015, 6 pages.
European Patent Office, Supplemental European Search Report for European Patent Application No. 09772630.1, dated Jan. 31, 2014, 8 pages.
European Patent Office, European Search Report for European Patent Application No. 14193392.9, dated Mar. 2, 2015, 8 pages.
Farquhar, et al., "Medical and Surgical management of Adenomyosis", Best Practice & Research Clinical Obstetrics and Gynaecology, vol. 20, No. 4, 2006, pp. 603-616.
Farquhar, "Management of Dysfunctional Uterine Bleeding", Drugs, vol. 44, No. 4, 1992, pp. 578-584.
Higham, et al., "The Medical Management of Menorrhagia", Br J Hosp Med. 45, Jan. 1991, pp. 19-21.
Hurskainen, et al., "Diagnosis and Treatment of Menorrhagia", Acta Obstetrica et Gynecologica Scandinavica, 86, 2007, pp. 749-757.
Japanese Patent Office, Decision of Rejection for Japanese Patent Application No. 2014-045808, Feb. 8, 2016, 8 pages.
Lethaby, et al., "Antifibrinolytics for heavy menstrual bleeding", Cochrane Database Syst. Rev. (4), Art. No. CD000249, 2000, 39 pages.
Lethaby, et al., "Nonsteroidal anti-inflammatory drugs for heavy menstrual bleeding", Cochrane Database Syst Rev. (1):CD000400, 2002, 2 pages.
Lethaby, et al., "Progesterone or progestogen-releasing intrauterine systems for heavy menstrual bleeding", Cochrane Database Syst Rev. Issue 4, Art. No. CD002126, Oct. 19, 2005, 66 pages.
Lethaby, et al., "Progesterone/progestogen releasing intrauterine systems for heavy menstrual bleeding", Cochrane Database Syst Rev. (2): CD002126, 2000, 41 pages.
Lumin, et al., "Pre-Clinical Experimental Studies of Indomethacin-Releasing Copper Intrauterine Device", Journal of Tongji Medical University, vol. 20, No. 3, 2000, pp. 249-252.
Luukkain En, et al., "Levonorgestrel-releasing IUD as a method of Contraception with Therapeutic Properties", Contraception, 52(5), 1995, pp. 269-276.
Mahgoub, "Levonorgestrel Releasing Contraception Devices", Papers Presented at the Symposium on Long-Acting Contraception, Nov. 3-4, 1983, pp. 174-179.
Moller, et al., "Expression of vascular endothelial growth factors and their receptors in human endometrium from women experiencing abnormal bleeding patterns after prolonged use of a levonorgestrel-releasing intrauterine system", Human Reproduction vol. 20, No. 5, 2005, pp. 1410-1417.
Rivera, et al., "Sustained intrauterine release of AMCA to reduce menstrual blood loss", Contraceptive Delivery Systems, vol. 5, No. 2, 1984, pp. 109-115.
Roberson, et al., "Contraception", Jul. 2003, 8 pages.
Robins, "Therapies for the Treatlllent of Abnorlllal Uterine Bleeding", Current Women's Health Reports 1(3), Dec. 2001, pp. 196-201.
Sitruk-Ware, et al., "The levonorgestrel intrauterine system: long-term contraception and therapeutic effects", Women's Health, 2005, 1(2), 2005, pp. 171-182.
Stewart, et al., "The effectiveness of the levonorgestrel-releasing intrauterine system in menorrhagia: a systematic review", British Journal of Obstetrics and Gynaecology, vol. 108, Jan. 2001, pp. 74-86.
Tauber, et al., "Reduced menstrual blood loss by release of an antifibrinolytic agent from intrauterine contraceptive devices", Am J Obstet Gynecol. 140(3), Jun. 1, 1981, pp. 322-328.
Taubert, et al., "Kontrazeption mit Hormonen", 2. uberarbeitete and erweiterte Auflage, Georg Thieme Verlag Stuttgart, New York, 1995, 10 pages.
Toppozada, et al., "Management of Uterine Bleeding by PGs or Their Synthesis Inhibitors", Advances in Prostaglandin and Thromboxane Research, vol. 8, 1980, pp. 1459-1463.
USPTO, Final Office Action for U.S. Appl. No. 13/934,913, dated Mar. 23, 2017, 17 pages.
USPTO, Non-final Office Action for U.S. Appl. No. 13/934,913, dated Jul. 15, 2015, 18 pages.
USPTO, Final Office Action for U.S. Appl. No. 13/934,913, dated Mar. 24, 2016, 24 pages.
USPTO, Non-final Office Action for U.S. Appl. No. 13/934,913, dated Oct. 6, 2016, 24 pages,
USPTO, Notice of Allowance for U.S. Appl. No. 13/934,913, dated Mar. 28, 2018, 8 pages.
Von Dadelszen, et al., "Increased Retention of Intrauterine Contraceptive Devices Medicated With Indomethacin and Medroxyprogesterone Acetate", Proceedings of the University of Otago Medical School, vol. 59, No. 3, 1981, pp. 101-103.
Wellington, et al., "Tranexamic Acid: A Review of its Use in the Management of Menorrhagia", Drugs 63(13), 2003, pp. 1417-1433.
Xue, et al., "Corrosion Behavior of Copper in a Copper Bearing Intrauterine Device in the Presence of Indomethacin", Contraception, 57, 1998, pp. 49-53.
Zhao, et al., "A Preliminary Morphometric Study on the Endometrium from Patients Treated with Indomethacin-Releasing Copper Intrauterine Device", Human Reproduction, vol. 12, No. 7, 1997, pp. 1563-1566.
USPTO, Final Office Action for U.S. Appl. No. 15/650,846, dated Apr. 5, 2019, 21 pages.

* cited by examiner

INTRAUTERINE DELIVERY SYSTEM FOR CONTRACEPTION

CROSS-REFERENCE TO RELATED APPLICATIONS

This application is a continuation application of U.S. patent application Ser. No. 13/934,913, filed Jul. 3, 2013 and titled "INTRAUTERINE DELIVERY SYSTEM FOR CONTRACEPTION," which is a continuation application of U.S. patent application Ser. No. 12/995,905, filed Dec. 2, 2010 and titled "INTRAUTERINE DELIVERY SYSTEM FOR CONTRACEPTION," which claims priority to International Patent Application No. PCT/FI2009/050598, filed Jul. 1, 2009 and titled "AN INTRAUTERINE DELIVERY SYSTEM FOR CONTRACEPTION," which claims priority to European Patent Application No. 08397516.9, filed Jul. 3, 2008 and titled "AN IMPROVED METHOD OF CONTRACEPTION," all of which are incorporated herein by reference.

SUMMARY

The present invention is related to an improved method of contraception, for preventing or suppressing abnormal and/or irregular endometrial bleeding and achieving a rapid induction of amenorrhea by using an intrauterine delivery system comprising progestogen, or a drug having a progestogenic activity, for the controlled release over a prolonged period of time and at a therapeutic level required for contraception, and a sufficient amount of one or more therapeutically active substances capable of suppressing abnormal and/or irregular endometrial bleeding.

The intrauterine delivery system comprises a body construction and at least one reservoir comprising a core and optionally a membrane encasing the core, the core and membrane essentially consisting of a same or different polymer composition, wherein said at least one reservoir comprises a progestogen, or a drug having a progestogenic activity, and one or more therapeutically active substances capable of suppressing abnormal and/or irregular endometrial bleeding or, wherein a progestogen or a drug having a progestogenic activity and said therapeutically active substance or substances capable of suppressing abnormal and/or irregular endometrial bleeding are in separate reservoirs.

BACKGROUND OF THE INVENTION

The publications and other materials used herein to illuminate the background of the invention, and in particular, cases to provide additional details respecting the practice, are incorporated by reference.

Bleeding disorders are one of the most frequent gynecological problems. The causes of bleeding disorders, and their frequency in particular, vary depending on the age of the woman affected. In premenopause and perimenopause, the most frequent causes are hormonal as well as organic changes in the uterus such as myomas, adenomyosis uteri, or endometrial polyps. Coagulation defects cause increased bleeding, particularly in girls and young women, with no other recognizable cause.

Dysfunctional uterine bleeding can be treated surgically or medically. Surgical treatment includes endometrial ablation of the first and second-generation, and hysterectomy. Medical treatment, with the avoidance of possibly unnecessary surgery is generally the first treatment option employed to treat excessive bleeding and the only option for those who wish to preserve their reproductive function.

Despite the availability of a number of drugs, there is a general lack of an evidence-based approach, marked variation in practice and continuing uncertainty regarding the most appropriate therapy. Adverse effects and problems with compliance also undermine the success of medical treatment.

Drugs used in the therapy, mostly administered orally, consist of compounds reducing menstrual bleeding such as anti-fibrinolytic agents, non-steroidal anti-inflammatory drugs, prostaglandin synthesis inhibitors, progestogens, estrogen-progestogen combinations (oral contraceptives, e.g.), danazol, or analogues of gonadotrophin releasing hormone.

Plasminogen activators are a group of enzymes that cause fibrinolysis (the dissolution of clots). An increase in the levels of plasminogen activators has been found in the endometrium of women with heavy menstrual bleeding compared to those with normal menstrual loss. Plasminogen activator inhibitors, i.e. antifibrinolytic agents and especially tranexamic acid, have therefore been used as a treatment for heavy menstrual bleeding (see for example Tauber et al., Am J Obstet Gynecol. 1981 Jun. 1; 140(3):322-8, Wellington et al., Drugs. 2003; 63(13):1417-33, Lethaby et al., Cochrane Database Syst. Rev. 2000; (4): CD000249, Bongers et al., Maturitas. 2004 Mar. 15; 47(3):159-74). There has been a reluctance to prescribe the required high oral dosages of tranexamic acid due to possible side effects of the drugs such as an increased risk of thrombogenic disease (deep venous thrombosis). Antifibrinolytic therapy seems to cause a greater reduction in objective measurements of heavy menstrual bleeding but is not associated with an increase in side effects when compared to placebo or other medical therapies (NSAIDS, oral luteal phase progestagens and ethamsylate).

Danazol is a synthetic steroid with anti-estrogenic and anti progestogenic activity, and weak androgenic properties. Danazol suppresses estrogen and progesterone receptors in the endometrium, leading to endometrial atrophy (thinning of the lining of the uterus) and reduced menstrual loss and to amenorrhoea in some women. Danazol appears to be an effective treatment for heavy menstrual bleeding compared to other medical treatments, though it is uncertain whether it is acceptable to women (see for example Robins, Curr Womens Health Rep. 2001 December; 1(3):196-201, Beaumont et al., Cochrane Database Syst Rev. 2002; (2): CD001017). The oral use of danazol may be limited by its side effect profile, its acceptability to women and the need for continuing treatment. Treatment with danazol caused a shorter duration of menstruation and more adverse events than NSAIDs but this did not appear to affect the acceptability of treatment.

Non-steroidal anti inflammatory drugs (NSAIDs) have proven useful in treating menorrhagia. NSAIDs reduce prostaglandin levels which are elevated in women with excessive menstrual bleeding and also may have a beneficial effect on dysmenorrhoea and headaches (see for example Lethaby et al., Cochrane Database Syst Rev. 2002; (1): CD000400). Furthermore, they are taken only during the duration of the menses and are relatively cheap. As a group, NSAIDs have shown to be less effective than either tranexamic acid or danazol.

In addition to their contraceptive effect, combined oral contraceptive pills can also lead to substantial reductions in blood loss. Birth control pills contain synthetic forms of estrogen and progesterone, which prevent ovulation and, thereby, reduce endometrial build-up or thickness. As a result, most of the oral contraceptive users have lighter or minimal menstrual bleeding. Several synthetic progestogens can balance the effects of estrogen normally produced by the body and reduce endometrial growth. Luteinizing hormone releasing hormone (LHRH) and gonadotropin-releasing hormone (GnRH) or their analogues also appear to reduce menstrual blood loss (see for example Higham, Br J Hosp Med. 1991 January; 45(1):19-21).

Some efforts have been done to treat gynaecological bleeding irregularities by using local administration, for example intrauterine implants and intrauterine devices.

European patents EP 24779 and EP 24781 relate to a use of an amidine derivatives or a mixture of amidines in conjunction with an intrauterine device to produce an antiproteolytic, an anti-fibrinolytic and anti-conceptive effect at a rate of 50 to 200 μg per day. International patent application WO 2006028431 relates to an intrauterine implant and methods of use for creating fibrosis and resulting in amenorrhea. In particular, the device relates to an easily deployed intrauterine implant that readily and consistently reduces or eliminates abnormal intrauterine bleeding. In addition, the device is also used as a uterine marker for visualizing endometrial tissue thickness and potential changes. The methods of this invention relate to therapeutic approaches and additional contraceptive action.

International patent application WO 98/14169 is related to methods and compounds for treatment of abnormal uterine bleeding by using compounds that block uterine stromal cell response to angiogenic growth factors by interfering with the growth factors themselves, or by inhibiting or blocking receptors in the uterine epithelial or stromal cells to those growth factors. The response-blocking compounds are introduced into the body of a patient either systemically or locally to the uterus, e.g., via medicated intrauterine devices. However, the application does not describe any practical examples of using these intrauterine devices to introduce the compounds.

Finally, the levonorgestrel-releasing intrauterine system (LNG-IUS, for example MIRENA, developed by Bayer Schering Pharma Oy, Turku, Finland) has been shown to be effective as such in the treatment of heavy menstrual blood losses (see for example Luukkainen et al., Contraception. 1995 November; 52(5): 269-76; Andersson et al., Br J Obstet Gynaecol. 1990 August; 97(8):690-4; Moller et al., Hum Reprod. 2005 May; 20(5):1410-7; Lethaby et al., Cochrane Database Syst Rev. 2005 Oct. 19; (4): CD002126 and Cochrane Database Syst Rev. 2000; (2): CD002126). The LNG-IUS is a systemic hormonal contraceptive that provides an effective method for contraception and complete reversibility, and has an excellent tolerability record. The low dosage of levonorgestrel released by the system ensures minimal hormone-related systemic adverse effects, which gradually diminish after the first few months of use. It also gives users non-contraceptive health benefits. The local release of levonorgestrel within the endometrial cavity results in strong suppression of endometrial growth as the endometrium becomes insensitive to ovarian estradiol. The endometrial suppression is the reason for a reduction in the duration and quantity of menstrual bleeding and alleviates dysmenorrhea. By reducing menstrual blood loss, the LNG-IUS increases the body iron stores and can therefore be used to effectively treat menorrhagia. In many menorrhagic women, use of these IUSs can replace more invasive surgical methods such as hysterectomy or endometrial resection.

During the first months of use of an IUS irregularity in vaginal bleeding patterns is the most common clinical side effect. The irregularities may include an increase in the menstrual blood loss at cyclical periods, increased duration of bleeding at periods, and intermenstrual bleeding and spotting. The pathogenesis of bleeding disturbances in IUS users is multifactorial and different etiologies have been suggested for different types of bleeding disturbances. Local increase in fibrinolytic activity is the most accepted cause for the increase of menstrual blood loss. The distortion of the endometrial vasculature by the presence of an intrauterine system can be explained by the direct effect of the device on the superficial vessels causing abrasions and erosions with possible irregular bleeding and/or the pressure distortion of the device, probably transmitted through endometrial tissue and resulting in endothelian injuries with the formation of fragile and dysfunctional blood vessels in the functional zone of the endometrium. The injury of vessel will lead to interstitial haemorrhage with the release of blood in an irregular pattern to the uterine cavity.

A significant number of users of the levonorgestrel-releasing intrauterine systems (LNG-IUS) expect not only contraceptive protection but also less menstrual problems. With LNG-IUS, there are undesired bleedings particularly during the first six to seven cycles after insertion. Complete amenorrhea is achieved only in part of the users even after longterm usage, and users often report about occasional bleedings, that are irregular and not predictable. Irregular bleeding is a common initial complaint among the users and longterm bleedings are often a reason for discontinuing the use of the system. Therefore there is still need for an intrauterine delivery system, the use of which would offer an improved and safe method of contraception and for suppressing abnormal and/or irregular bleeding and achieving a rapid induction of amenorrhea.

OBJECT AND SUMMARY OF THE INVENTION

The object of the present invention is to provide an improved method of contraception and for preventing or suppressing abnormal and/or irregular bleeding and achieving a rapid induction of amenorrhea by using an intrauterine delivery system comprising progestogen, or a drug having a progestogenic activity, for the controlled release over a prolonged period of time and at a level required for contraception, and a sufficient amount of one or more therapeutically active substances capable of suppressing abnormal and/or irregular endometrial bleeding. The intrauterine delivery system comprises a body construction and at least one reservoir comprising a core and optionally a membrane encasing the core, the core and membrane essentially consisting of a same or different polymer composition, wherein said at least one reservoir comprises a progestogen, or a drug having a progestogenic activity, and one or more therapeutically active substances capable of suppressing abnormal and/or irregular endometrial bleeding or, wherein a progestogen, or a drug having a progestogenic activity, and said therapeutically active substance or substances capable of suppressing abnormal and/or irregular endometrial bleeding are in separate reservoirs.

The object of the invention is further to provide a contraceptive intrauterine system with clinically relevant improvements and a method for treating undesirable and/or abnormal intrauterine bleeding.

The object is particularly to provide an intrauterine system having a high success rate at providing earlier onset of reliably stable amenorrhea and having minimal to no side-effects or related complications.

In general, the present invention contemplates an intrauterine delivery system providing a method which not only enhances the anti-fertility action of the system but also provides reduction or elimination of abnormal or excessive bleeding, such as spotting or menorrhagia, for an extended period of time as well as reduces menstrual complaints, such as dysmenorrhea and premenstrual symptoms. Avoiding undesired menstrual bleeding always means also avoiding symptoms associated with menstrual bleeding such as dysmenorrhea and premenstrual symptoms. Some of the proposed compounds can also reduce bleeding problems in women with van Willebrand disease.

By using the intrauterine delivery system an anti-proteolytic action and a decrease of the prostaglandin activity in the endometrium and/or muscle wall of the uterus can reduce the risk of expulsion.

The therapeutically active substance capable of preventing or suppressing abnormal and/or irregular endometrial bleeding can be used in dosages that are much lower compared to the systemic treatment yet without loosing its efficacy. Since synergistic effects between progestogens and these additional compounds can be assumed, further dose reductions are possible. Therefore, the risk of undesired systemic effects would be extremely low. An atrophic endometrium could further increase the contraceptive reliability.

Thus the present invention concerns a method, a delivery system and use as described below in the independent claims.

BRIEF DESCRIPTION OF THE FIGURES

The invention is further illustrated by the following figures describing a common T-shaped frame as an example of an intrauterine system and various constructions of the reservoir according to the invention.

DETAILED DESCRIPTION

Figure 1:
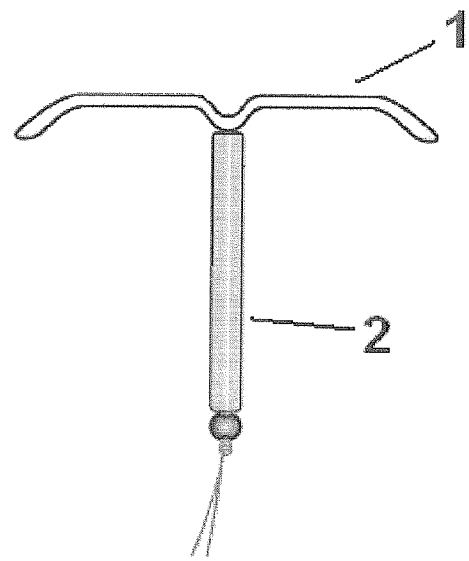
FIG. 1 illustrates an intrauterine system comprising a body (1), and a reservoir (2) containing therapeutically active agent(s).
Figure 2:
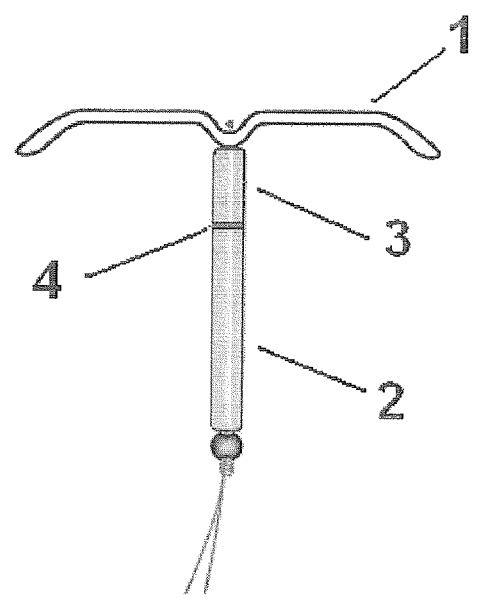
FIG. 2 illustrates an intrauterine system comprising a body (1), and two reservoirs (2 and 3) being positioned one on the other and separated by a separation membrane or a metal ring (4)
Figure 3:
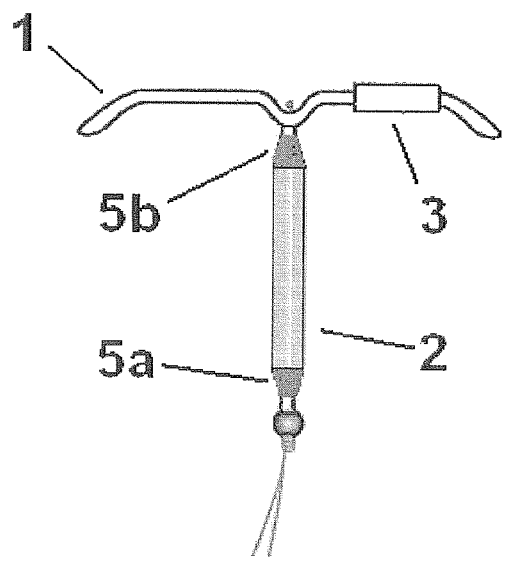
FIG. 3 illustrates an intrauterine system comprising a body (1), and two reservoirs (2 and 3) attached at different parts of the body. Reservoir (2) is held at the correct position by locking means (5a and 5b).
Figure 4:
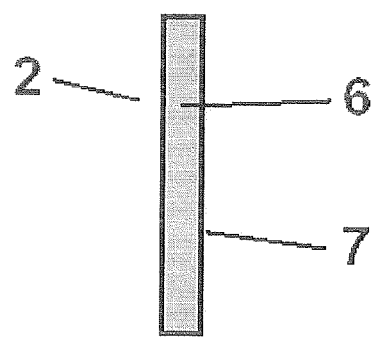
FIG. 4 illustrates a reservoir of an intrauterine system (2) comprising a core (6) containing a therapeutically active substance or substances and encased by a membrane (7).
Figure 5:
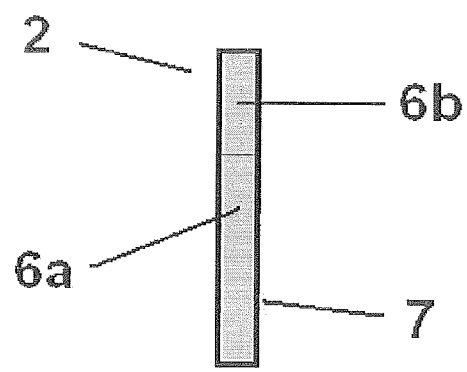
FIG. 5 illustrates a reservoir of an intrauterine system (2) comprising two core segments (6a and 6b) attached one on the other, each containing same or different therapeutically active substance or substances and encased by a membrane (7).
Figure 6:
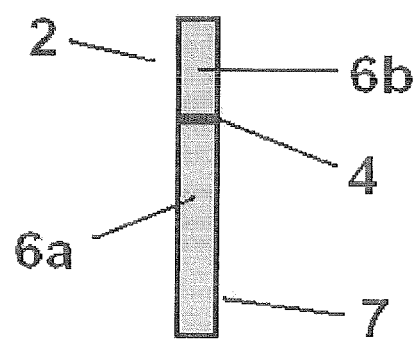
FIG. 6 illustrates a reservoir of an intrauterine system (2) comprising two core segments (6a and 6b), each containing same or different therapeutically active substance or substances and encased by a membrane (7). The segments are separated from each other by a separation membrane (4).
Figure 7:
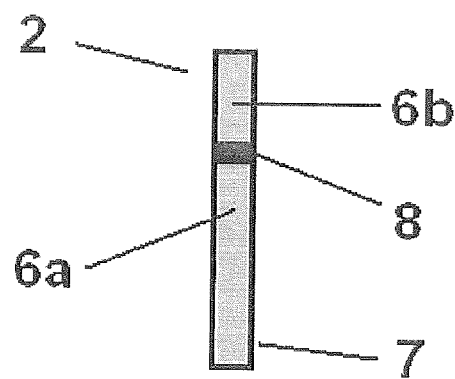
FIG. 7 illustrates a reservoir of an intrauterine system (2) comprising two core segments (6a and 6b), each containing a same or different therapeutically active substance or substances and encased by a membrane (7). The segments are separated from each other by an inert placebo segment (8).
Figure 8:
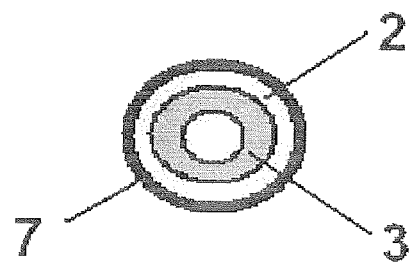
FIG. 8 illustrates a cross section of an assembly where two reservoirs (2 and 3) are positioned one inside the other, the assembly being encased by a membrane (7).

The object of the present invention is to provide a method of contraception and for preventing or suppressing abnormal and/or irregular endometrial bleeding and achieving a rapid induction of amenorrhea by using an intrauterine delivery system comprising a progestogen, or a drug having a progestogenic activity, for the controlled release over a prolonged period of time and at a level required for contraception, and a sufficient amount of one or more therapeutically active substances capable of suppressing abnormal and/or irregular endometrial bleeding.

According to an embodiment of the invention the intrauterine delivery system comprises a body construction and at least one reservoir comprising a core and optionally a membrane encasing the core, said core and membrane essentially consisting of a same or different polymer composition, wherein at least one reservoir comprises a progestogen or a drug having a progestogenic activity and at least one reservoir comprises a therapeutically active substance or substances capable of suppressing abnormal and/or irregular endometrial bleeding. The intrauterine delivery system has an uncomplicated design and can be prepared by an economically attractive manufacturing process.

According to another embodiment the intrauterine delivery system consists of a body construction and one reservoir comprising a core and optionally a membrane encasing the core, said core and membrane essentially consisting of a same or different polymer composition, wherein the reservoir comprises a progestogen, or a drug having a progestogenic activity, and a therapeutically active substance or substances capable of suppressing abnormal and/or irregular endometrial bleeding.

According to a further embodiment the intrauterine delivery system consists of a body construction and at least two reservoirs comprising a core and optionally a membrane encasing the core, said core and membrane essentially consisting of a same or different polymer composition, wherein one reservoir comprises a progestogen or a drug having a progestogenic activity, and the other reservoir comprises a therapeutically active substance or substances capable of suppressing abnormal and/or irregular endometrial bleeding.

The core comprises essentially a polymer composition, that is, the core is a polymer matrix wherein the therapeutically active substance or substances are dispersed. The polymer compositions are chosen according to the release rates desired. The release rates can be controlled by the membrane or by the membrane together with the core, but the release rate can also be controlled by the core alone. Therefore, even in the case there is no membrane or when the membrane primarily regulating the release of the therapeutically active substance would be damaged, the substance or substances would not be released in a completely uncontrolled manner thus causing side effects to the patient.

The polymer composition of the core and/or the membrane can be chosen so that the intrauterine system releases a sufficient predetermined amount of both progestogen, or a compound having progestogenic activity, and a therapeutically active substance capable of suppressing and/or preventing abnormal and/or irregular endometrial bleeding. By using the intrauterine system according to the invention it is possible even to deliver sufficient daily amounts of water soluble substances, for example such as tranexamic acid, which has not shown to be possible by using the prior art intrauterine systems.

According to the embodiment in which the delivery system consists of two or more reservoirs, said reservoirs may be positioned separately on the body of the intrauterine system.

They may also be positioned one inside the other or one on the other, in which case they may be attached next to each other or may be separated from each other by a separation membrane or by an inert placebo compartment.

According to the embodiment in which said at least two therapeutically active substances are in the same reservoir, the substances may be homogeneously mixed in the core material. The core may also comprise more than one segment or part, for example two, three, four or five segments or parts consisting of a same or different polymer composition. At least one of these segments comprises a progestogen, or a drug having a progestogenic activity, or one or more therapeutically active substances capable of suppressing abnormal and/or irregular endometrial bleeding.

One or more of the segments may be an inert separation membrane or a placebo segment without any therapeutically active substance.

An advantage of using a separation membrane or an inert placebo segment to separate reservoirs or core segments from each other is, that the release rates are more easily controllable since there is no or only a minimal interaction between the active substances. The material and the thickness of a separation membrane or of a placebo segment depend on the capacity of the material to prevent permeation of the active substances. Most ideally the separation membrane or the placebo segment completely prevents mixing of the active substances, which otherwise might disturb the release pattern. Any combination of structure is naturally possible and within the scope of the invention.

The membrane may cover the whole reservoir or cover only a part of the system, for example one segment of the core, whereby the degree of extension can vary depending on a number of factors, for example such as the choice of materials and the choice of active substances. The polymer composition used in the membrane is such that it allows the predetermined, constant release rates of the therapeutically active agents. The thickness of the membrane depends on materials and active substances used as well as on desired release profiles, but generally the thickness is smaller than the thickness of the core member.

The membrane may consist of more than one layer. Each layer has a certain thickness, and the thickness of the layers may be the same or different. The combination of different membrane layers either in thickness or in material or both, gives a further possibility for controlling the release rates of the active agents.

Polymer compositions, namely the polymer compositions of the core, the membrane and the possible separation membrane or the inert placebo segment, can be the same or different and may stand for one single polymer, or the polymer composition may be made up of two or more polymers.

In principle any polymer, either biodegradable or non-biodegradable, can be used as long as it is biocompatible. As known in the art, the release kinetics of a therapeutically active agent from a polymer based delivery system depends on the molecular weight, solubility, diffusivity and charge of the therapeutically active agent as well as on the characteristics of the polymer, on the percentage of the loading of the therapeutically active agent, on the distance the therapeutically active agent must diffuse through the device body to reach its surface and on the characteristics of any matrix or membrane.

Polysiloxanes, in particular poly(dimethyl siloxane) (PDMS), are highly suitable for use as a membrane or matrix regulating the permeation rate of drugs. Polysiloxanes are physiologically inert, and a wide group of therapeutically active substances are capable of penetrating polysiloxane membranes, which also have the required strength properties. The permeation rate of the therapeutically active substances can be adjusted at a desired level by modifying the polymeric material in a suitable way, e.g. by adjusting hydrophilic or hydrophobic properties of the material. It is for example known from the literature that addition of poly (ethylene oxide) groups or trifluoropropyl groups to a PDMS polymer change the permeation rate of therapeutically active substances.

Further examples of suitable materials include, but are not limited to, copolymers of dimethylsiloxanes and methylvinylsiloxanes, ethylene/vinyl acetate copolymers (EVA), polyethylene, polypropylene, ethylene/propylene copolymers, acrylic acid polymers, ethylene/ethyl acrylate copolymers, polytetrafluoroethylene (PTFE), polyurethanes, thermoplastic polyurethanes and polyurethane elastomers, polybutadiene, polyisoprene, poly(methacrylate), polymethyl methacrylate, styrene-butadiene-styrene block copolymers, poly(hydroxyethyl-methacrylate) (pHEMA), polyvinyl chloride, polyvinyl acetate, polyethers, polyacrylonitriles, polyethylene glycols, polymethylpentene, polybutadiene, polyhydroxy alkanoates, poly(lactic acid), poly(glycolic acid), polyanhydrides, polyorthoesters, hydrophilic polymers such as the hydrophilic hydrogels, cross-linked polyvinyl alcohol, neoprene rubber, butyl rubber, hydroxyl-terminated organopolysiloxanes of the room temperature vulcanizing type which harden to elastomers at room temperature following the addition of cross-linking agents in the presence of curing catalysts, one- or two-component dimethylpolysiloxane compositions cured by hydrosilylation at room temperature or under elevated temperatures, as well as mixtures thereof. It is also clear for an expert in the field that suitable materials may be composed of the copolymers of the above mentioned homopolymers.

The structural integrity of the material may be enhanced by the addition of a particulate material such as silica or diatomaceous earth. The elastomers can also be mixed with other additives to adjust elastomer's hydrophilic or hydrophobic properties while taking into account that all additives need to be biocompatible and harmless to the patient. The core or the membrane may also comprise additional material to further adjust the release rate of one or several of the therapeutic substances, for example complex forming agents such as cyclodextrin derivatives to adjust the initial burst of the substance to the accepted or desired level. Auxiliary substances, for example such as tensides, anti-foaming agents, solubiusers or absorption retarders, or a mixture of any two or more of such substances, can also be added in order to impart the desired physical properties to the body of the delivery system.

According to an embodiment, the core and the membrane are made of a siloxane based elastomer composition comprising at least one elastomer and possibly a non-crosslinked polymer.

The term "elastomer composition" may stand for one single elastomer, the deformation of which caused by the strain is reversible so that the elastomer's shape recovers to a certain level after the strain. The elastomer composition may also be made up of two or more elastomers blended with each other.

The term "siloxane-based elastomer" shall be understood to cover elastomers made of poly (disubstituted siloxanes) where the substituents mainly are lower alkyl, preferably alkyl groups of 1 to 6 carbon atoms, or phenyl groups, wherein said alkyl or phenyl can be substituted or unsubstituted. A widely used and preferred polymer of this kind is poly(dimethylsiloxane) (PDMS).

The elastomer composition may be selected from the group consisting of
  an elastomer composition comprising poly(dimethylsiloxane) (PDMS),
  an elastomer composition comprising a siloxane-based elastomer comprising 3,3,3-trifluoropropyl groups attached to the silicon atoms of the siloxane units,
  an elastomer composition comprising poly(alkylene oxide) groups, said poly(alkylene oxide) groups being present as alkoxy-terminated grafts or blocks linked to the polysiloxane units by silicon-carbon bonds or as a mixture of these forms, and
  a combination of at least two thereof.

According to a preferred embodiment of the invention, in the siloxane-based elastomer from 1 to approximately 50% of the substituents attached to the silicon atoms of the siloxane units are 3,3,3-trifluoropropyl groups. The percentage of the substituents that are 3,3,3-trifluoropropyl groups can be for example 5-40%, 10-35%, 1-29% or 15-49.5%. The term "approximately 50%" means that the degree of 3,3,3-trifluoropropyl substitution is in fact somewhat below 50%, because the polymer must contain a certain amount (about 0.15% of the substituents) of cross-linkable groups such as vinyl or vinyl-terminated groups.

According to another preferred embodiment of the invention, the siloxane-based elastomer comprises poly(alkylene oxide) groups so that the poly(alkylene oxide) groups are present in the said elastomer either as alkoxy-terminated grafts of polysiloxane units or as blocks, said grafts or blocks being linked to the polysiloxane units by silicon-carbon bonds. Preferably poly(alkylene oxide) groups mentioned above are poly(ethylene oxide) (PEO) groups.

The methods for the preparation of suitable polymers are given for example in international patent applications WO 00/00550, WO 00/29464 and WO 99/10412 (each assigned to Leiras Oy).

The Therapeutically Active Agent

Progestogen can be any therapeutically active substance having progestogenic activity enough to achieve contraception. In a further embodiment, the progestogenic compound is a steroidal progestogenic compound. Examples of suitable progestogenic compounds include compounds such as progesterone and its derivatives, cyproterone acetate, desogestrel, etonogestrel, levonorgestrel, lynestrenol, medroxyprogesterone acetate, norethisterone, norethisterone acetate, norgestimate, drospirenone, gestodene, 19-nor-17-hydroxy progesterone esters, 17α-ethinyltestosterone and derivatives thereof, 17α-ethinyl-19-nortestosterone and derivatives thereof, ethynodiol diacetate, dydrogesterone, norethynodrel, allylestrenol, medrogestone, norgestrienone, ethisterone and dl-norgestrel.

In a particular embodiment the progestogenic compound is levonorgestrel. Other progestogens than levonorgestrel with pronounced angiostatic features could be used in combination with the drugs mentioned above.

Therapeutically active substances that can be used in conjunction with the invention to prevent or suppress endometrial bleeding can, without limiting the scope of the invention, be selected from the group of prostaglandin synthesis inhibitors like diclofenac sodium, NSAIDs, such as naproxen, indomethacin, ibuprofen, mefenamic acid, flurbiprofen, inhibitors of leukotriene, e.g. zafirlukast and montelukast and its salts, oxytocin antagonists, pancreatic trypsin inhibitors like Trasylol, COX-inhibitors, antifibrinolytic drugs, such as tranexamic acid and precursors thereof, aminocapronic acid, PAI-1, desmopressin, clomiphene citrate, p-aminomethyl-benzoic acid, estrogens, antiestrogens, aromatase inhibitors, cytokine inhibitors, glucocorticoids, progestogens with pronounced glucocorticoid acticity, danazol and gestrinone.

The above mentioned drugs are to some extend already used for systemic treatment of hypermenorrhea. Moreover, it may be possible to use also inhibitors of angiogenesis, such as angiostatin, endostatin.

The release of progestin should preferably last for from one up to ten years, or from one to five years, or preferably from three to five years, and the release of additional drugs should last for at least from a week to the maximum of five years, or from a week to one year, or preferably form a week to six months.

The amount of a therapeutically active substances incorporated in the delivery system, both the progestogen and the therapeutically active substance capable of preventing or suppressing endometrial bleeding, varies depending on the particular therapeutically active agent and the time for which the intrauterine system is expected to provide therapy. There is no critical upper limit on the amount of therapeutically active agent incorporated in the device since, depending on the selected body construction, the size, shape and number of reservoirs for administering dosages can be varied and modified. The lower limit depends on the efficacy of the therapeutically active agent and the expected release time.

The delivery system according to the invention provides sufficient amounts and rates of release of said therapeutically active compounds for use in contraception and/or hormone therapy and for suppressing or preventing endometrial bleeding. By these sufficient amounts and rates for release is understood that throughout the release period needed, at each point in time a safe and sufficient effective amount of the compounds are released. In particular the release profile of the progestogenic compound may not be too steep. The mean release required is dependent on the use. In an even further embodiment for use in contraception the mean release may also not be too low. A person skilled in the art is readily able to determine the amount of the therapeutically active agent needed for each specific application of the delivery system.

Therapeutic dosages of active substances reducing menstrual bleeding are to be adapted due to their local activities on the endometrium. Significantly lower dosages than needed for the systemic application are sufficient if released by the intrauterine system. These lower dosages must be in the range of pharmacological equivalency to total dosages of 4-6 g of tranexamic acid administered orally per day.

Preferably, the amount of progestogen or a substance having a progestogenic activity, as well as the amount of the therapeutically active substance capable of preventing or suppressing endometrial bleeding vary from almost zero to 60 wt-%, when it is mixed into the core matrix, the preferred amount being between 5-50 wt-%. Other possible ranges of the amount of the therapeutically active agent are 0.5-60 wt-%, 5-55 wt-%, 10-50 wt-%, 25-60 wt-%, 40-50 wt-% and 5-40 wt-%.

Manufacture of the Intrauterine Delivery Systems

The shape and size of the delivery system discussed in this application may be chosen by the person skilled in the art within the dimensions of the uterine cavity. It is also evident that the systems according to the invention may be designed to apply to human as well as to animal mammals.

An intrauterine delivery system preferably comprises a body forming the frame of the system and a reservoir or reservoirs containing therapeutically active substances attached on the body. A commonly used intrauterine system is a T-shaped object fabricated of any biocompatible material and consisting of an elongate member having at one end a transverse member comprising two arms, the elongate member and the transverse member forming a substantially T-shaped piece when the system is positioned in the uterus. The medicated reservoir or reservoirs can be attached to the elongate member, to the transverse member or members, or both to the elongate member and the transverse member(s). The body of the intrauterine system may naturally have various other forms, for example continuous curved shapes, like circular, angular, oval-shaped, shield shaped or polygonal, as long as their shape and size fit to the size and geometry of the endometrial cavity.

The manufacturing of these systems is discussed below, even though it is well known in the art.

The body and the reservoir(s) may be manufactured simultaneously or separately followed by their assembly. The body may preferably be manufactured by injection or compression moulding. The drug containing cores can be manufactured by mixing the therapeutically active substance or substances within the core matrix material for example such as polydimethylsiloxane (PDMS) or the components forming the polymer composition as defined above, processed to the desired shape by moulding, casting, extrusion, or by any other appropriate methods known in the art.

The membrane layer, if any, can be applied onto the core according to known methods such as by using extrusion or injection moulding methods, spraying or dipping. As an alternative, the prefabricated membrane tube can be expanded mechanically for example with a suitable device or by using for example pressurized gas, such as air, or by swelling it in a suitable solvent, such as cyclohexane, diglyme, isopropanol, or in a mixture of solvents, where after the swollen membrane tube is mounted onto the core. When the solvent evaporates, the membrane tightens on the core.

The reservoir can be fixed on the frame by using different methods. The frame may for example comprise an elongated extension in the form of a metal or polymer shaft, core, rod or pin or the like at a suitable point on which the hollow tube-like reservoir is assembled, preferably by first enlarging the diameter of the reservoir tube to some degree, for example by using pressure or solvent swelling, and thereafter by simply sliding the reservoir onto the extension or inserting the extension into the hollow reservoir. It is also possible to assemble first the hollow tube-like core onto the body and then assemble the membrane onto the core. Other methods to attach the reservoir to the frame include for example known techniques of welding, use of an adhesive, or use of special metal or polymer inserts, clips, connectors, adapters, clothespin-type means or clamps or like.

If needed, one or each end of the reservoirs so obtained may be sealed by using known techniques, for example by applying a drop of an adhesive or silicon glue.

The delivery system can also be manufactured by coating the body with the drug containing core material by using known technology, for example such as dipping, spraying, injection molding and like. According to the embodiment where the reservoirs are inside one another, the delivery system may for example be manufactured by coating the body first with a progestogen containing polymer layer followed optionally a membrane layer, and then coating the system with a polymer layer comprising a therapeutically active substance capable of preventing or suppressing endometrial bleeding, and if needed, followed by a outer membrane layer.

The reservoirs, the cores of which consist of several parts or segments, can also be prepared for example by using a coextrusion method described in the Finnish patent FI 97947. A therapeutically active substance is mixed within the core matrix polymer composition, and processed to the desired shape and size by using known extrusion methods. The membrane layer may then be applied onto the prefabricated cores by feeding each of the core segments to the extruder followed either by another segment without any active ingredient or by leaving an empty space filled with air between the segments, which during the extrusion process will be filled with the membrane material to form a separation membrane.

The body of the system may further comprise specific locking means to keep the cores or reservoirs in place during the insertion step, during the use of the device or during the removal of the device. To improve the visualization and the detection of the intrauterine system for example in X-ray or an ultrasound examination, the system may comprise inert metal clips, rings or sleeves on the body or on the reservoir, or an inert metal coating on at least part of the body, or metal powder, metal particles or X-ray contrast agents mixed with the raw materials of the body, core matrix or membrane of the system during the compounding step, or anchoring a metallic loop to the body of an IUS.

The delivery system according to the invention can be manufactured in any size as required, the exact size being dependent on the mammal and particular application. In practice, the dimensions of the delivery system should be close to the size of the uterine cavity. For a human female the length of the IUS body is normally in the order of from 20 to 40 mm. in length, preferably from 25 to 38 mm and the width of the body is in the order of from 20 to 32 mm corresponding generally to the width of the fundal portion of the endometrial cavity. The cross-sectional diameter of the body member is in the order of from 1 to 4 mm, preferably from 1.5 to 3 mm.

The lengths of the cores of the drug delivery system are chosen to give the required performance. Ratios of the core lengths will depend upon the particular therapeutic application, including the desired ratio and dosage of each drug to be delivered. The length of the reservoir as well as of a core segment can be for example from 1 to 35 mm. The length of a placebo segment separating the reservoirs or core segments may generally vary between 1-5 mm and depends on the nature of the material and its capacity to prevent permeation of the active materials.

The thickness of a separation membrane can be about 0.2 to 5 mm. The thickness, i.e. the outer diameter of the core or core segment, can be from 0.1 to 5.0 mm, and preferably from 0.2 to 3.5 mm. The thickness of the membrane encasing the core or core segment is from 0.1 to 1.0 mm, preferably from 0.2 to 0.6 mm.

EXPERIMENTAL PART

The invention is described below in greater detail in the following, non-limiting examples.

Example 1

Core Preparation 45 parts by weight of levonorgestrel, 10 parts by weight of tranexamic acid and 50 parts by weight of poly(dimethylsiloxane-co-vinylmethylsiloxane) and 1.2 parts by weight of dichlorobenzoylperoxide-polydimethylsiloxane paste (50% of dichlorobenzoylperoxide) were mixed with a 2-roll mill. The mixture was extruded to a tube-like form with a wall thickness of 0.8 mm and outer diameter of 2.8 mm and cured by heat at +150° C. for 15 minutes, during which crosslinking took place. The crosslinked core was cut into 24 mm length.

Preparation of the Delivery System

The core was swollen in cyclohexane and pulled over the IUS body. Cyclohexane was allowed to evaporate.

Example 2

Core Preparation 50 parts by weight of levonorgestrel, 50 parts by weight of poly(dimethylsiloxane-co-vinylmethylsiloxane) and 1.2 parts by weight of dichlorobenzoylperoxide-polydimethylsiloxane paste (50% of dichlorobenzoylperoxide) were mixed with a 2-roll mill. The mixture was extruded to a tube-like form with a wall thickness of 0.8 mm and outer diameter of 2.8 mm and cured by heat at +150° C. for 15 minutes, during which crosslinking took place. The crosslinked core was cut into 15 mm length.

Second core was prepared in a similar manner by using 10 parts by weight of danazol in place of levonorgestrel. The crosslinked core was cut into 8 mm length.

Membrane Preparation 99 parts of silica-filled poly(dimethylsiloxane-co-vinylmethylsiloxane), 10 ppm Pt-catalyst (of the reaction species) and 0.03 parts of inhibitor (ethynyl cyclohexanol) and approximately 0.6 parts of poly(hydrogenmethylsiloxane-co-dimethylsiloxane) crosslinker were mixed in a 2-roll mill. Based on the method described in FI 97947, the membrane material was coextruded to a tube-like form by simultaneously inserting the above prepared two cores through the inner nozzle in the die by leaving an empty space between the cores to be filled by membrane material. The wall thickness of the membrane was 0.23 mm. The thickness of the separation membrane formed between the cores was 1.8 mm.

Example 3

Core Preparation 54 parts of commercial poly(dimethylsiloxane-co-vinylmethylsiloxane), 45.5 parts by weight of levonorgestrel, 0.4 parts of poly(hydrogenmethylsiloxane-co-dimethylsiloxane) crosslinker, 0.02 parts of ethynyl cyclohexanol inhibitor and 10 ppm of Pt-catalyst (of the reaction species) in vinyl-methyl-siloxane were mixed in a kneating mill. The mixture was extruded to a tube-like form with a wall thickness of 0.7 mm and cured by heat at +115° C. for 30 minutes and cooled.

Second core was prepared in a similar manner by using 79.5 parts of commercial poly(dimethylsiloxane-co-vinylmethylsiloxane) and in place of levonorgestrel 20 parts by weight of mefenamic acid.

Membrane Preparation 9 parts of α,ω-divinylether terminated poly(ethylene oxide)-b-poly(dimethylsiloxane) multiblock copolymer (PEO-b-PDMS), 89 parts of silica-filled poly(dimethylsiloxane-co-vinylmethylsiloxane), 10 ppm Pt-catalyst (of the reaction species), 0.03 parts inhibitor (ethynyl cyclohexanol), and approximately 2 parts of poly(hydrogenmethylsiloxane-co-dimethylsiloxane) crosslinker were mixed in a two-roll mill. The mixture was extruded to a tube-like form with a wall thickness of 0.2 mm and cured by heat.

Preparation of the Delivery System

The membrane was swollen in isopropanol and pulled over both cores. Isopropanol was allowed to evaporate. Levonorgestrel containing reservoir was cut to the length of 22 mm and mefenamic acid containing reservoir to the length of 4 mm. Next the tube-like reservoirs were swollen in cyclohexane and assembled on the vertical stem of a T-shaped body by separating the reservoirs form each other by a silver ring having essentially the inner diameter of the vertical stem and outer diameter just slightly smaller than the outer diameter of the reservoirs. Cyclohexane was again allowed to evaporate.

Example 4

Core Preparation 29 parts of PEO-b-PDMS, 29 parts of poly(dimethylsiloxane-covinylmethylsiloxane), 10 ppm Pt-catalyst (of the reaction species), 0.02 parts inhibitor (ethynyl cyclohexanol), and approximately 2.4 parts of poly(hydrogenmethylsiloxane-co-dimethylsiloxane) crosslinker were mixed in a two-roll mill and 39 parts of levonorgestrel was added. The mixture was extruded to a tube-like form with a wall thickness of 0.8 mm and outer diameter of 2.8 mm and cured by heat at +150° C. for 15 minutes, during which crosslinking took place. The crosslinked core was cut into 12 mm length.

Second core was prepared in a similar manner by using 20 parts by weight of mefenamic acid in place of levonorgestrel. The crosslinked core was cut into 10 mm length. Third core, a placebo segment, was prepared in a similar method but without adding any active substance. The crosslinked core was cut into 3 mm length.

Membrane Preparation 9 parts of PEO-b-PDMS, 89 parts of silica-filled poly(dimethylsiloxane-co-vinylmethylsiloxane), 10 ppm Pt-catalyst (of the reaction species), 0.03 parts inhibitor (ethynyl cyclohexanol), and approximately 2 parts of poly-(hydrogenmethylsiloxane-co-dimethylsiloxane) crosslinker were mixed in a two-roll mill. The membrane material was coating extruded on the above prepared three cores by successively inserting them through the inner nozzle (in the order of levonorgestrel core, placebo, mefenamic acid core) in the die. The formed wall thickness of the membrane was 0.22 mm.

Example 5

Core Preparation 24 parts of PEO-b-PDMS, 24 parts of poly(dimethylsiloxane-covinylmethylsiloxane), 10 ppm Pt-catalyst (of the reaction species), 0.02 parts inhibitor (ethynyl cyclohexanol), and approximately 2.4 parts of poly-(hydrogenmethylsiloxane-co-dimethylsiloxane) crosslinker were mixed in a two-roll mill and 35 parts of levonorgestrel and 14.5 parts of mefenamic acid was added. The mixture was extruded to a tube-like form with a wall thickness of 0.8 mm and outer diameter of 2.8 mm and cured by heat at +150° C. for 15 minutes, during which crosslinking took place. The crosslinked core was cut into 24 mm length.

Membrane Preparation 100 parts by weight of silica-filled poly(trifluoropropylmethylsiloxane-co-vinylmethylsiloxane), in which the content of trifluoropropyl-methylsiloxane units was 99 mol-%; i.e. degree of trifluoropropyl substitution was 49.5%, and 1.2 parts by weight of dichlorobentsoylperoxide-polydimethylsiloxane paste (50% of dichlorobenzoylperoxide) were mixed with a 2-roll mill. The mixture was extruded into a tube-like form with a wall thickness of 0.22 mm and cured by heat.

Preparation of the Delivery System

The membrane was swollen in isopropanol and pulled over the core. Solvent was allowed to evaporate. Next the tube-like reservoir was swollen with cyclohexane and assembled on a T-shaped IUS body. Cyclohexane was again allowed to evaporate. The ends of the reservoir were sealed by using silicone glue.

Preparation of the Delivery System, Examples 2 and 4

The core-membrane reservoir was swollen in cyclohexane and the stem of the body was inserted into the hollow reservoir. Cyclohexane was again allowed to evaporate.

Drug Release Test

The release rate of the drug from the implant was measured in vitro as follows:

The intrauterine delivery systems were attached into a stainless steel holder in vertical position and the holders with the devices were placed into glass bottles containing 250 ml of a dissolution medium. The glass bottles were shaken in shaking water bath 100 rpm at 37° C. The dissolution medium was withdrawn and replaced by a fresh dissolution medium at predetermined time intervals, and the amount of the released drug was analysed by using standard HPLC methods. The concentration of the dissolution medium and the moment of change (withdrawal and replacement) of medium were selected so that sink-conditions were maintained during the test.

Although the invention has been described in terms of particular embodiments and applications, one of ordinary skill in the art can in light of this teaching generate additional embodiments and modifications without departing from the spirit of or exceeding the scope of the claimed invention. Accordingly, it is to be understood that the drawings and descriptions herein are offered by way of example to facilitate comprehension of the invention and should not be construed to limit the scope thereof.

The invention claimed is:

1. A method for contraception and suppressing abnormal or irregular endometrial bleeding that is observed during use of a levonorgestrel compound containing intrauterine delivery system comprising the step of administering to a patient in need thereof the intrauterine delivery system comprising:
    a body construction forming a T-shaped frame, the T-shaped frame including an elongate member at one end and a transverse member comprising two arms, a first drug reservoir on the elongate member and a second drug reservoir on the elongate member, wherein the first drug reservoir and the second drug reservoir are each surrounded by locking means to keep the first drug reservoir and the second drug reservoir, respectively, in place during insertion of the intrauterine delivery system and wherein the first drug reservoir is coated by a membrane,
    the levonorgestrel compound located in the first drug reservoir and being present in an amount required for contraception, and
    indomethacin located in the second drug reservoir, which is not coated by the membrane, the indomethacin being present at an amount capable of suppressing abnormal or irregular endometrial bleeding that is observed during the use of the levonorgestrel containing intrauterine delivery system.

2. The method according to claim 1, wherein the indomethacin is present at the amount capable of suppressing abnormal or irregular endometrial bleeding that occurs during a first six months after insertion of the intrauterine delivery system.

3. The method according to claim 1, wherein the intrauterine delivery system further comprises at least one of an inert metal clip, a ring, a sleeve, an insert metal coating, metal powder, metal particles, and a metallic loop that make the intrauterine delivery system visible in an x-ray or during an ultrasound examination.

4. The method according to claim 1, wherein the membrane is from 0.1 to 1.0 mm thick.

5. The method according to claim 1, wherein a length of the first drug reservoir and the second drug reservoir are from 1 to 35 mm.

6. The method according to claim 1, wherein a length of the body construction is from 20 to 40 mm.

7. The method according to claim 1, wherein a cross-sectional diameter of the body construction is from 1 to 4 mm.

8. The method according to claim 1, wherein the locking means includes at least one of an adhesive, a metal insert, a polymer insert, a clip, a connector, an adaptor, a clothespin-type means, and a clamp.

9. The method according to claim 1, wherein the indomethacin is present at the amount capable of suppressing abnormal or irregular endometrial bleeding that occurs during a first six months after insertion of the intrauterine delivery system.

10. The method according to claim 1, wherein the intrauterine delivery system further comprises at least one of an inert metal clip, a ring, a sleeve, an insert metal coating, metal powder, metal particles, and a metallic loop that make the intrauterine delivery system visible in an x-ray or during an ultrasound examination.

11. The method according to claim 1, wherein the membrane is from 0.1 to 1.0 mm thick.

12. The method according to claim 1, wherein a length of the first drug reservoir and the second drug reservoir are from 1 to 35 mm.

13. The method according to claim 1, wherein a length of the body construction is from 20 to 40 mm.

14. The method according to claim 1, wherein a cross-sectional diameter of the body construction is from 1 to 4 mm.

15. The method according to claim 1, wherein the locking means includes at least one of an adhesive, a metal insert, a polymer insert, a clip, a connector, an adaptor, a clothespin-type means, and a clamp.

16. An intrauterine delivery system (IUS) comprising:
    a body construction forming a T-shaped frame, the T-shaped frame including an elongate member at one end and a transverse member comprising two arms, a first drug reservoir on the elongate member and a second drug reservoir on the elongate member, wherein the first drug reservoir is surrounded by locking means to keep the first drug reservoir and the second drug reservoir, respectively, in place during insertion of the intrauterine delivery system and wherein the first drug reservoir is coated by a membrane, a levonorgestrel compound located in the first drug reservoir and being present in an amount required for contraception, and indomethacin located in the second drug reservoir, which is not coated by the membrane, the indomethacin being present at an amount capable of suppressing abnormal or irregular endometrial bleeding that is observed during a use of the intrauterine delivery system.

17. The IUS of claim 16, wherein the indomethacin is present at the amount capable of suppressing abnormal or irregular endometrial bleeding that occurs during a first six months after insertion of the IUS.

18. IUS of claim 16, wherein the intrauterine delivery system further comprises at least one of an inert metal clip, a ring, a sleeve, an insert metal coating, metal powder, metal particles, and a metallic loop that make the intrauterine delivery system visible in an x-ray or during an ultrasound examination.

19. IUS of claim 16, wherein the membrane is from 0.1 to 1.0 mm thick.

20. IUS of claim 16, wherein a length of the first drug reservoir and the second drug reservoir are from 1 to 35 mm.

21. IUS of claim 16, wherein the second drug reservoir is surrounded by the locking means to keep the second drug reservoir in place.

* * * * *